US006838090B2

(12) United States Patent
Tabibi et al.

(10) Patent No.: US 6,838,090 B2
(45) Date of Patent: Jan. 4, 2005

(54) WATER-INSOLUBLE DRUG DELIVERY SYSTEM

(75) Inventors: S. Esmail Tabibi, Rockville, MD (US); Emmanuel I. Ezennia, Baltimore, MD (US); B. Rao Vishnuvajjala, Rockville, MD (US); Shanker Gupta, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/455,295

(22) Filed: Jun. 5, 2003

(65) Prior Publication Data

US 2003/0211144 A1 Nov. 13, 2003

Related U.S. Application Data

(62) Division of application No. 09/868,858, filed as application No. PCT/US99/30631 on Dec. 22, 1999, now Pat. No. 6,682,758.
(60) Provisional application No. 60/113,423, filed on Dec. 22, 1998.

(51) Int. Cl.$^7$ .............................................. A61K 9/127

(52) U.S. Cl. ...................... 424/450; 264/4.1; 264/4.3; 264/4.6

(58) Field of Search .................. 424/450; 264/4.1, 264/4.3, 4.6; 514/937–943

(56) References Cited

U.S. PATENT DOCUMENTS

| | | | |
|---|---|---|---|
| 4,565,806 A | 1/1986 | Setälä | |
| 4,684,630 A | 8/1987 | Repta et al. | |
| 4,737,323 A | 4/1988 | Martin et al. | |
| 4,816,247 A | 3/1989 | Desai et al. | |
| 4,826,689 A | 5/1989 | Violanto | |
| 4,842,856 A | 6/1989 | Hoederath et al. | |
| 4,997,454 A | 3/1991 | Violante et al. | |
| 5,039,527 A | 8/1991 | Tabibi et al. | |
| 5,077,057 A | 12/1991 | Szoka, Jr. | |
| 5,091,188 A | 2/1992 | Haynes | |
| 5,270,053 A | 12/1993 | Schneider et al. | |
| 5,516,770 A | 5/1996 | Waranis et al. | |
| 5,530,006 A | 6/1996 | Waranis et al. | |
| 5,616,330 A | 4/1997 | Kaufman et al. | |
| 5,616,341 A | 4/1997 | Mayer et al. | |
| 5,616,587 A | 4/1997 | François et al. | |
| 5,616,588 A | 4/1997 | Waranis et al. | |
| 5,656,296 A | 8/1997 | Khan et al. | |
| 5,672,358 A | 9/1997 | Tabibi et al. | |
| 5,690,954 A | 11/1997 | Illum et al. | |
| 5,714,520 A | 2/1998 | Jones et al. | |
| 5,731,356 A | 3/1998 | Jones et al. | |
| 5,736,159 A | 4/1998 | Chen et al. | |

FOREIGN PATENT DOCUMENTS

| | | |
|---|---|---|
| BE | 893949 | 11/1982 |
| DE | 41 25 255 | 2/1993 |
| DE | 41 25 255 A1 | 2/1993 |
| EP | 214501 | 3/1987 |
| EP | 215313 | 3/1987 |
| EP | 502766 | 9/1992 |
| EP | 0 648 494 | 4/1995 |
| EP | 0 720 853 | 7/1996 |
| EP | 770387 | 5/1997 |
| FR | 2 609 631 | 7/1988 |
| WO | WO 98/53799 | 12/1998 |

OTHER PUBLICATIONS

Eiseman et al., "#536 Pharmacokinetics of 17–allylamino(17demethoxy)geldanamycin in SCID mice bearing MDA–MB–453 xenografts and alterations in the expression of p185$^{arb-B2}$ in the xenografts following treatment", AACR–NCI–EORTC International Conference, Nov. 16–19, 1999, Washington, DC.

Eiseman et al., "#2063 Plasma pharmacokinetics and tissue distribution of 17–allylaminogeldanamycin (NSC 330507), a prodrug for geldanamycin, in DC$_2$F$_1$ mice and Fisher 344 rats", Proceedings of the American Association for Cancer Research, vol. 38, Mar. 1998, p. 308.

Page et al., #2067 Comparison of geldanamycin (NSC–122750) and 17–allylaminogeldanamycin (NSC0330507D) toxicity in rats, Proceedings of the American Association for Cancer Research, vol. 38, Mar. 1998, p. 308.

Egorin et al., "#3567 Metabolism of 17–(allylamino)–17–demethoxygeldanamycin (17AAG) (NSC 330507) by murine and human hepatic preparations", Proceedings of the American Association for Cancer Research, vol. 38, Mar. 1998, p. 524.

Burger et al., "#504 Antitumor activity of 17–allylaminogeldanamycin (NSC 330507) in melanoma xanografts in associated with decline in Hsp90 protein expression", 10$^{th}$ NCJ–EDRTC Symposium on New Drugs in Cancer Therapy, Jun. 16–19, 1999, Amsterdam.

Laurie McCarthy, "Nanonization" Technology Provides Solutions for the Insoluble, http://news.pharmaceuticalonlin.com/feature–articles/19980113–72.html.

"KODAK Established Independent Business to Develop Small Particle Technology", http://www.kodak.com/about-Kodak/corpInfo/pressReleases/pr951106–2.shtml.

(List continued on next page.)

Primary Examiner—Gollamudi S. Kishore
(74) Attorney, Agent, or Firm—Leydig, Voit & Mayer, Ltd.

(57) ABSTRACT

The present invention provides a drug delivery system comprising a water-insoluble drug, a water-miscible organic solvent for the water-insoluble drug, a surfactant, and water, as well as a process for preparing the same. This invention further provides a pharmaceutical composition comprising a pharmaceutically acceptable carrier and such a drug delivery system. In addition, the present invention provides a method of delivering a drug to a host by administering to the host the drug delivery system of the present invention.

8 Claims, No Drawings

OTHER PUBLICATIONS

"Nanoparticles", Process and Characteristics, Formulations and Biodistribution, and Case Studies, http://www/sts-duotek.com/nanoport.htm © 1997–98.

Davis, "Biomedical applications of nanotechnology–implications for drug targeting and gen therapy", Trends Biotechnol, Jun. 1997, 15(6):217–214 (Abstract only).

Sharma et al., "Novel taxol formulations: preparation and characterization of taxol–containing liposome", Pharm Res, Jun. 1994, 11(6):889–896 (Abstract only).

Hauss et al., Lipid–based delivery systems for improving the ioavailability and lymphatic transport of a poorly water–woluble LTB4 inhibitor, J Pharm Sci, Feb. 1998, 87(2):164–169 (Abstract only).

Merisko–Liversidge et al., "Formulation and antitumor activity evaluation of nonocrystalline suspensions of poorly soluble anticancer drugs", Parm Res, Feb. 1996, 13(2):272–278 (Abstract only).

Anderson et al., "Strategies in he design of solution–stable, water–soluble prodrugs II: properties of micellar prodrugs of methylprednisolone", J Pharm Sci, Apr. 1985, 74(4):375–381 (Abstract only).

Storm et al., "Colloidal systems for tumor targeting", Hybridoma, Feb. 1997, 16(1):119–125 (Abstract only).

Jones, "The surface properties of phospholipid liposome systems and their characterization", Adv colloid Interface Sci, Jan. 3, 1995, 54:93–128 (Abstract only).

Storm et al., Biopharmaceutical aspects of lipid formulations of amphotericin B., Eur J Clin Microbiol Infect Dis, Jan. 1997, 16(1):64–73 (Abstract only).

Benita et al., "Submicron emulsions as colloidal drug carriers for Intravenous administration: comprehensive physicochemical characterization", J Pharm Sci, Nov. 1993, 82(11):1069–1079 (Abstract only).

Gabizon, "Tailoring liposomes for cancer drug delivery: from the bench to the clinic", Ann Biol Clin (Paris), 1993, 51(9):811–813 (Abstract only).

Marty et al., Nanoparticles—a new colloidal drug delivery system., Pharm Acta Helv, 1978, 53(1):17–23 (Title only).

Thompson, "Cyclodextrins—enabling excipients: Their present and future use in pharmaceuticals", Critical Reviews in Therapeutic Drug Carrier Systems (USA), 1997, 14/1 (1–104) (Abstract only).

Sculier et al., "Intravenous Infusion of high doses of liposomes containing NSC 251635, a water–insoluble cytostatic agent. A pilot study with pharmacokinetic data", J. Clin. Oncol. (USA), 1986, 4/5 (789–797), (Abstract only).

Torchilin et al., "Long acting thrombolytic immobilized enzymes", J. Control. Release (Netherlands), 1985, vol. 2 (321–330) (Abstract only).

Laduron et al., "Chemotherapeutic efficacy of Nocodazole (Reg. Trademark) encapsulated in liposomes on L1210 murine leukemia", Res. Commun. Chem. Pathol. Pharmacol. (USA), 1983, 39/3 (419–436) (Abstract only).

Alyautdin et al., "Delivery of loperamide across the blood–brain–barrier with polysorbate 80–coated polybutylcyanoacrylate nanoparticles", Pharmaceutical Research (New York) 14(3), 1997, 325–328 (Abstract only).

Leroux et al., "Pharmacokinetics of a novel HIV–1 protease inhibitor Incorporated into biodegradable or enteric nanoparticles following intravenous and oral administration to mice", Journal of Pharmaceutical Sciences (J–Pharm–Sci) 84:1387–1391, Dec. 1995 (3 pages).

Page et al., "Comparison of geldanamycin (NSC0122750) and 17–allylaminogeldanamycin (NSC–330507D) toxicity in rats", Proc Annu Am Assoc Cancer Res, 38:A2067 1997 (Abstract only).

Eiseman et al., "Plasma pharmacokinetics and tissue distribution of 17–allylaminogeldanamycin (NSC–330507), a prodrug for geldanamycin, in DC2F1 mice and Fisher 344 rats", Proc Annu Am Assoc Cancer Res, 38:A2063 1977 (Abstract only).

Larroque et al., "Serum albumin as a vehicle for zinc phthalocyanine: photodynamic activities in solid tumour models", Br J Cancer, 1996, 74(12):1886–90 (Abstract only).

Merisko–Liversidge et al., "Formulation and antitumor activity evaluationof nanocrystalline suspensions of poorly soluble anticancer drugs", Pharm Res, 13(2):272–8 1996 (Abstract only).

Son, "Intravenous delivery of water–insoluble drugs", Diss Absr Int [B], 52(5):2518 1991 (Abstract only).

Zuidam et al., "Sterilization of liposomes by heat treatment", Pharm Res, 10(11):1591–6 1993 (Abstract only).

Tiurin–Kuz'Min et al., "Vliianie davleniia metabolicheski inertnykh gazov I temperatury na tekuchest' membran liposomov" Aviakosm Ekolog Med, 26(1):31–3 1992 (Abstract only).

Chen, "The preparation of monoclonal antiboby HI30–homoharringtonine liposomes (immunoliposomes) and targeting tests in vitro", Chung Kuo I Hsueh Ko Hsueh Yan Hsueh Pao, 13(5):323–6 1991.

WATER-INSOLUBLE DRUG DELIVERY SYSTEM

This patent application is a divisional of U.S. patent application Ser. No. 09/868,858, filed Jun. 21, 2001 now U.S. Pat. No. 6,682,758, which is the national phase of PCT/US99/30631, filed Dec. 22, 1999, which claims the benefit of U.S. Provisional Patent Application No. 60/113,423, filed Dec. 22, 1998.

TECHNICAL FIELD OF THE INVENTION

The present invention relates to a drug delivery system for water-insoluble drugs, in particular, 17-allylaminogeldanamycin and carboxyamidotriazole, to a method of delivering a drug to a host, and to a pharmaceutical composition comprising such a drug delivery system.

BACKGROUND OF THE INVENTION

Difficulties exist in developing safe and sterile intravenous formulations of sparingly water-soluble (i.e., water-insoluble) compounds. One such compound is 17-allylaminogeldanamycin (17-AAG) which is under development for clinical use as an anticancer agent because of it's unique mechanism of action as a modulator of HSP-90. This compound was selected for clinical studies based on its in vitro activity against chemorefractory tumor and novel biological actions. Its effect on the depletion of the erB-2 gene product p185 has been reported (Miller et al., Cancer Res., 54, 2724–30 (1994)). Another such compound is carboxyamidotriazole (CAI) which is currently under development for clinical use as an antitumor agent based on its antiangiogenic and antimetastatic effects.

Delivery systems for water-insoluble compounds have been developed using lipid vesicles and oil-in-water type emulsions (Ogawa et al., U.S. Pat. No. 5,004,756; Tabibi et al., U.S. Pat. No. 5,039,527; Cotter, U.S. Pat. No. 5,461,037; Lundquist, U.S. Pat. No. 5,660,837, Tabibi et al., U.S. Pat. No. 5,672,358). However, these formulations require complicated processing steps, and the presence of non-aqueous solvents such as dimethylsulfoxide (DMSO) causes physical instability in the formulation. For example, the complete removal of organic solvent in the processing of the liposomes has been reported to be very important to the stability of the vesicles of some systems (Vemuri et al., Acta Helvetica, 70(2), 95–111 (1995)). Other methods are said to require high-speed homogenization of the phospholipids with the active ingredient followed by complete evaporation of the organic solvent with vigorous stirring to achieve optimal entrapment of the active ingredient (Xu et al., Pharm. Research, 7(5), 553–57 (1990)). Likewise, it has been demonstrated that the addition of organic solvents to oil-in-water type emulsions causes the oil droplets to coalesce, resulting in instability (Li et al., Pharmaceutical Research, 10(4), 535–41 (1993)).

Thus, there is a need for a more satisfactory delivery system for water-insoluble drugs. The present invention provides such a drug delivery system that incorporates an organic solvent, desirably without adversely affecting the physical stability of the surfactant within the aqueous medium. The present invention also provides methods of preparing and using such a drug delivery system. These and other benefits and advantages of the present invention will be apparent from the description of the present invention herein.

BRIEF SUMMARY OF THE INVENTION

The present invention provides a drug delivery system comprising a water-insoluble drug, a water-miscible organic solvent for the water-insoluble drug, a surfactant, and water, wherein the water-insoluble drug is dissolved in the water-miscible organic solvent that forms a continuous phase with the water that contains the surfactant. The present invention further provides a pharmaceutical composition comprising a pharmaceutically acceptable carrier and the drug delivery system of the present invention. In addition, the present invention provides a method of delivering a drug to a host by administering the drug delivery system of the present invention to the host.

The present invention also provides a process for the preparation of a drug delivery system comprising (a) providing a drug solution comprising a water-insoluble drug and a water-miscible organic solvent for the water-insoluble drug, (b) providing a surfactant solution comprising a surfactant and water, and (c) combining the drug solution and the surfactant solution to provide a drug delivery system.

DETAILED DESCRIPTION OF THE INVENTION

The present invention provides a drug delivery system for water-insoluble compounds, in particular, a drug delivery system for 17-AAG and CAI, and methods of preparing and using such a drug delivery system.

For the purposes of describing the present invention, the term "drug" means any compound which is biologically active, e.g., exhibits a therapeutic or prophylactic effect in vivo, or a biological effect in vitro. The term "water-insoluble" as used in conjunction with the present invention encompasses the terms sparingly water-soluble, slightly or very slightly water-soluble, and practically or totally water-insoluble compounds (Remington: the Science and Practice of Pharmacy, vol. 1, 194–195 (Gennaro, ed., 1995)). A compound is water-insoluble for the purposes of this invention if it requires at least 30 parts solvent to dissolve one part solute (Id.). The term "water-miscible" as used in conjunction with the present invention means susceptible of being mixed with, and forming a continuous phase with, water. The term "isotonizing agent" is used to refer to any compound or composition capable of changing the osmotic pressure of a solution. Concentrations expressed as "percent weight in volume" (% w/v) refer to the number of grams of solute in 100 ml of solution. The term "particle size" is used in the context of the present invention to refer to the average diameter of particles, e.g., lipid vesicles, in a suspension.

Drug Delivery System

The drug delivery system of the present invention is comprised of a water-insoluble drug, a water-miscible organic solvent for the water-insoluble drug, a surfactant, and water. The water-insoluble drug is dissolved in the water-miscible organic solvent. The water-insoluble organic solvent forms a continuous phase with the water, which water contains the surfactant. The drug delivery system provided by the present invention is physically and chemically stable. Thus, the components of the-system will not micro-crystallize or precipitate when stored at approximately 20° to 30° Celsius for up to 24 hours.

Any water-insoluble drug, or combination of drugs including at least one water-insoluble drug, can be used in conjunction with the present invention. Suitable drugs include antihypertension drugs, antibiotic drugs, and anti-cancer or antitumor drugs. The present invention is particularly useful with the water-insoluble drugs geldanamycin, especially 17-AAG, and CAI.

Any suitable water-miscible organic solvent can be used in conjunction with the present invention. Selection of a suitable organic solvent will depend in part upon the solubility of the particular drug in the solvent, the degree to which the solvent is miscible in water, and the toxicity of the solvent. The solvent desirably is physiologically acceptable. Examples of solvents that may be used in conjunction with the present invention include, but are not limited to, dimethylsulfoxide (DMSO), dimethylacetamide (DMA), dimethylformamide, various alcohols such as ethanol, glycols, glycerin, propylene glycol, and various polyethylene glycols. It is preferred that the solvent be DMSO or DMA.

Any suitable surface active agent (surfactant) can be used in the context of the present invention. The surfactant desirably is physiologically acceptable. Physiologically acceptable surfactants are generally known in the art and include various detergents and phospholipids. It is preferred that the surfactant is a phospholipid such as, but not limited to, an egg phospholipid, a vegetable oil phospholipid such as a soybean phospholipid, or phosphatidylcholine. Most preferably, the surfactant is an egg phospholipid.

The surfactant is typically present in a concentration of about 0.5–25% w/v based on the amount of the water and/or other components into which the surfactant is dissolved. Preferably, the surfactant is present in a concentration of about 0.5–10% w/v, most preferably about 1–4% w/v. It is further preferred that the surfactant form vesicles having an average particle size of about 50–200 nm, more preferably about 100–150 nm. A method by which this can be accomplished is set out below. Average particle size can be determined by known methods, for example, by laser light scattering technique.

It is preferred that an isotonizing agent be used in conjunction with the present inventive drug delivery system. The isotonizing agent can be any reagent capable of adjusting the osmotic pressure of the suspension of the present invention to a value nearly equal to that of a body fluid. The isotonizing agent desirably is physiologically acceptable. Examples of isotonizing agents include glycerol, sugar alcohols such as sobitol and xylitol, monosaccharides such as glucose and fructose, disaccharides such as maltose and dextrose, and amino acids such as L-alanine, L-valine, and glycine. It is preferred that the isotonizing agent is dextrose or glycerin.

Pharmaceutical Composition

The present inventive pharmaceutical composition comprises a carrier, preferably a pharmaceutically acceptable carrier, and a drug delivery system of the present invention. The pharmaceutical composition can comprise more than one active ingredient, such as a single drug delivery system with two or more drugs, two or more drug delivery systems, or one or more drug delivery systems in conjunction with one or more drugs (e.g., water-soluble drugs) independent of the drug delivery system(s). The carrier can be any suitable carrier or mixture of carriers.

The pharmaceutically acceptable carrier can be any of those conventionally used and is limited only by chemico-physical considerations, such as solubility and lack of reactivity with the active compound(s), as well as by the route of administration. It is preferred that the pharmaceutically acceptable carrier be one which is chemically inert to the active compound(s) and one which has no detrimental side effects or toxicity under the conditions of use. Suitable pharmaceutically acceptable carriers, for example, vehicles, adjuvants, excipients, and diluents, are well-known in the art and are readily available.

There are a wide variety of suitable formulations of the pharmaceutical composition of the present invention. The following formulations for oral, aerosol, parenteral, subcutaneous, intravenous, intramuscular, interperitoneal, rectal, and vaginal administration are merely exemplary and are in no way limiting.

Injectable formulations are among those formulations that are preferred in accordance with the present inventive method. The requirements for effective pharmaceutical carriers for injectable compositions are well known to those of ordinary skill in the art (see, e.g., *Pharmaceutics and Pharmacy Practice*, J. B. Lippincott Company, Philadelphia, Pa., Banker and Chalmers, eds., pages 238–250 (1982), and *ASHP Handbook on Injectable Drugs*, Trisell, 4th ed., pages 622–630 (1986)). Such injectable compositions desirably are administered intravenously, intratumorally (within a tumor), or peritumorally (near the outside of a tumor).

Formulations suitable for parenteral administration include isotonic sterile injection solutions, which can contain anti-oxidants, buffers, bacteriostats, and solutes that render the formulation isotonic with the blood of the intended recipient, and sterile suspensions that can include suspending agents, solubilizers, thickening agents, stabilizers, and preservatives. Suitable pharmaceutically acceptable carriers for parenteral administration include a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1, 3-dioxolane-4-methanol, ethers, such as poly (ethyleneglycol) 400, an oil, a fatty acid, a fatty acid ester or glyceride, or an acetylated fatty acid glyceride with or without the addition of a further, pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral.

Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-b-aminopropionates, and 2-alkylimidazoline quaternary ammonium salts, and (e) mixtures thereof.

The parenteral formulations will typically contain from about 0.5 to about 25% by weight of the active ingredient in solution. Preservatives and buffers may be used. In order to minimize or eliminate irritation at the site of injection, such compositions may contain one or more nonionic surfactants, in addition to those used in the drug delivery system of the present invention, having a hydrophile-lipophile balance (HLB) of from about 12 to about 17. The quantity of surfactant in such formulations will typically range from about 5 to about 15% by weight. Suitable such surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials. Extemporaneous injection solutions and suspensions can be prepared from sterile powders, granules, and tablets of the kind previously described.

Topical formulations are well-known to those of skill in the art. Such formulations are particularly suitable in the context of the present invention for application to skin.

Formulations suitable for oral administration can consist of (a) liquid solutions, such as an effective amount of the present inventive drug delivery system dissolved in diluents, such as water, saline, or orange juice, (b) capsules, sachets, tablets, lozenges, and troches, each containing a predetermined amount of the active ingredient, as solids or granules, (c) powders, (d) suspensions in an appropriate liquid, and (e) suitable emulsions. Liquid formulations may include diluents, such as water and alcohols, for example, ethanol, benzyl alcohol, and the polyethylene alcohols. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The present inventive drug delivery system, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

Additionally, the present inventive drug delivery system can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

Method of Delivering a Drug to a Host

The present inventive drug delivery system can be used for any suitable purpose. For example, the present inventive drug delivery system can be used for scientific and research purposes, such as in determining the types of diseases or disorders, particularly cancers, which can be treated and for which their onset can be delayed, or progression slowed, by administration of the present inventive drug delivery system (s). The present inventive drug delivery system can be used in vitro in conjunction with cultured cells, tissues, organs, and the like.

The present inventive drug delivery system also provides a method of delivering a drug to a host and has particular usefulness in applications in vivo. For example, the present inventive drug delivery system can be used in the prevention, delay of onset, slowing, or treatment of the progression of a disease or disorder, such as cancer.

The present inventive method of delivering a drug to a host, especially an animal such as a mammal, preferably a human, comprises administering the drug delivery system of the present invention (e.g., a composition comprising the drug delivery system of the present invention) to a host. Preferably, the drug delivery system is administered in an amount effective to treat or prevent a disease or disorder in the host (e.g., a therapeutically or prophylatically effective amount).

The method of delivering a drug to a host through administering the drug delivery system of the present invention can be made more effective in the treatment or prevention of disease by using it in conjunction with other known methods of treating or preventing diseases or disorders. For example, the present inventive method of treating cancer through administering an anticancer or antitumor effective amount of the drug delivery system of the present invention utilizing an anticancer or antitumor drug can be made more effective by administering one or more other anticancer or antitumor compounds along with the drug delivery system of the present invention. These other anticancer compounds include, but are not limited to, all of the known anticancer compounds approved for marketing in the United States and those that will become approved in the future. See, for example, Table 1 and Table 2 of Boyd, *Current Therapy in Oncology*, Section I. Introduction to Cancer Therapy (J. E. Niederhuber, ed.), Chapter 2, by B. C. Decker, Inc., Philadelphia, 1993, pp. 11–22. More particularly, these other anticancer compounds include doxorubicin, bleomycin, vincristine, vinblastine, VP-16, VW-26, cisplatin, procarbazine, and taxol for solid tumors in general; alkylating agents, such as BCNU, CCNU, methyl-CCNU and DTIC, for brain or kidney cancers; and antimetabolites such as 5-FU and methotrexate for colon cancer.

One skilled in the art will appreciate that suitable methods of administering compositions comprising the present inventive drug delivery system to a host, especially an animal such as a mammal, in particular a human, are available, and, although more than one route can be used to administer a particular composition, a particular route can provide a more immediate and more effective reaction than another route. Accordingly, the herein-described methods are merely exemplary and are in no way limiting.

The dose administered to an animal, such as a mammal, in particular a human, should be sufficient to prevent the targeted disease or disorder, e.g., cancer, delay its onset, slow its progression, or treat the disease or disorder (e.g., reverse or negate the condition). One skilled in the art will recognize that dosage will depend upon a variety of factors including the strength of the particular composition employed, as well as the age, species, condition, and body weight of the animal. The size of the dose will also be determined by the route, timing, and frequency of administration as well as the existence, nature, and extent of any adverse side-effects that might accompany the administration of a particular composition and the desired physiological effect.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. The present inventive method will typically involve the administration of about 0.1 to about 100 mg (e.g., about 1 to about 50 mg) of one or more of the drugs described above per kg body weight of the host.

Preparation Process

The present invention provides for a process of producing a drug composition comprising (a) providing a drug solution comprising a water-insoluble drug and a water-miscible organic solvent for the water-insoluble drug, (b) providing a surfactant solution comprising a surfactant and water, and (c) combining the drug solution and the surfactant solution to provide a drug delivery system. The components utilized in the present inventive process as well as additional desirable and/or optimal components are described above with respect to the present inventive drug delivery system.

The surfactant solution can be prepared by hydrating the surfactant in water to form relatively large structured particles. It is preferred that the surfactant solution is further processed, prior to combination with the drug solution, to provide a vesicle suspension having an average particle size between 50 and 200 nm, preferably between 100 and 150 nm. This can be accomplished using a high speed mixing device, particularly an ultra high energy mixing device such as, for example, a Microfluidizer® device. Microfluidizer equipment is commercially available from Microfluidics Corp., Newton Mass., and is described in U.S. Pat. No. 4,533,254.

It is also preferred that the drug solution and the surfactant solution are independently sterilized prior to their combination. The individual sterile solutions can be stored or transported separately, and combined to provide a drug delivery system at any time. Sterilization of the solutions can be performed by any technique known in the art, for example, by passing each solution through a sterilizing membrane filter. For the purposes of the present invention, each solution is preferably sterilized using a 0.22 μm pore rated sterile filter prior to the combination of the solutions.

The following examples illustrate the present invention, but, of course, should not be construed as limiting the scope of the invention in any way.

EXAMPLES

Examples 1 through 7 illustrate the preparation of drug delivery systems for the water-insoluble drug 17-AAG. Examples 8 and 9 illustrate the preparation of drug delivery systems for the water-insoluble compound (CAI). Example 10 illustrates the use of a drug delivery system to deliver a water-insoluble drug to a mammal. In each example, the surfactant solution formed 100–125 nm vesicles in the final product as determined by laser light scattering technique.

Example 1

A 4% w/v surfactant solution comprising relatively small lipid vesicles was prepared by completely hydrating 2 g egg phospholipids in 48 ml double distilled water and passing it through a Microfluidizer® device. The solution was sterilized using a 0.22 μm pore rated sterile filter. A drug solution having a drug concentration of 50 mg/ml was prepared by dissolving 100 mg of 17-AAG into 2 ml of dimethylsulfoxide (DMSO). This solution was also passed through a 0.22 μm pore rated sterile filter. The drug solution was added to the surfactant solution resulting in a clear colloidal suspension.

The product suspension was divided into two portions for analysis. The first portion was analyzed for drug concentration by high performance liquid chromatography (HPLC). The second portion was filtered through a 0.22 μm pore rated filter, and the filtrate was analyzed for drug concentration by HPLC. No difference in the drug concentration between the two samples was observed, indicating that no microcrystals or precipitate formed during or after the preparation. Both portions of the product solution were kept at room temperature (about 25° C.) for 24 hours. The previously filtered portion was filtered again and analyzed by HPLC. No change in drug concentration was observed, indicating that no microcrystal formation or precipitation had occurred after 24 hours.

Example 2

The procedure described in Example 1 was repeated using a drug solution having a 17-AAG concentration of 25 mg/ml in DMSO. The final product was physically and chemically stable.

Example 3

The procedure described in Example 1 was repeated using a surfactant solution having a phospholipid concentration of 3% w/v. The final product was physically and chemically stable.

Example 4

The procedure described in Example 1 was repeated using a surfactant solution having a phospholipid concentration of 2% w/v. The final product was physically and chemically stable.

Example 5

The procedure described in Example 1 was repeated using a surfactant solution having a phospholipid concentration of 2% w/v and using dimethyl acetamide (DMA) as the water-miscible organic solvent. The final product was physically and chemically stable.

Example 6

The procedure described in Example 1 was repeated using a surfactant solution having a phospholipid concentration of 1% w/v and using dimethyl acetamide (DMA) as the water-miscible organic solvent. The final product was physically and chemically stable.

Example 7

The procedure described in Example 1 was repeated using a surfactant solution having a phospholipid concentration of 2% w/v and further comprising 5% w/v dextrose. The final product was physically and chemically stable.

Example 8

The procedure described in Example 1 was repeated using a drug solution comprising 100 mg/ml of CAI (NSC-609974) in DMSO. The final product was physically and chemically stable.

Example 9

The procedure described in Example 1 was repeated using a drug solution comprising 100 mg/ml of CAI (NSC-609974) in DMSO, and a surfactant solution having a phospholipid concentration of 4% w/v and further comprising 2.2% w/v glycerin. The final product was physically and chemically stable.

Example 10

A drug delivery system was prepared using a surfactant solution having a phospholipid concentration of 4% w/v and a drug solution comprising 25 mg/ml of 17-AAG. The solutions were combined using the procedure described in Example 1 to yield a drug delivery system having a final drug concentration of 4 mg/ml. The drug delivery system was administered in a single intravenous dose of 40 mg/kg to normal SCID (severe combined immunodeficiency) mice and to SCID mice bearing human breast cancer xenografts. The concentrations of 17-AAG and its major metabolite (17-AG) were measured using high performance liquid chromatography (HPLC), and the levels of HSP90, HSP70, and p185 were measured using western blot analysis. The concentrations of 17-AAG and 17-AG in normal tissues were below detection levels at 7-hours post-administration, but remained detectable in tumor tissue at a concentration of about 0.5–1 $\mu$g/g for more than 48 hours after administration. HSP90 and HSP70 concentrations in the tumor tissue of the treated mice were lower than in untreated mice at 4-hours and 7-hours after administration, but were elevated at 48-hours and 72-hours after administration. Expression of p185 in the xenografts of the treated mice was increased 2-fold over expression in untreated mice at 2-hours after administration, but was 30% below control levels at 7-hours, 24-hours, and 48-hours after administration. This example demonstrates that an effective amount of a water-insoluble drug can be successfully administered to a mammal using the drug delivery system of the present invention.

All publications cited herein are hereby incorporated by reference to the same extent as if each publication was individually and specifically indicated to be incorporated by reference and was set forth in its entirety herein.

While the foregoing invention has been described in some detail for purposes of clarity and understanding, it will be appreciated by one skilled in the art from a reading of this disclosure that various changes in form and detail can be made without departing from the true scope of the invention.

What is claimed is:

1. A vesicular drug delivery system comprising
   (a) a drug solution comprising a water-insoluble drug selected from the group consisting of 17-allylaminogeldanamycin and carboxyamidotriazole dissolved in a pharmaceutically acceptable, water-miscible organic solvent, and
   (b) a surfactant suspension comprising water and 0.5% to 10% (w/v) of a surfactant, wherein said surfactant forms vesicles having an average particle size from 50 nm to 200 nm,
   wherein the drug solution and the surfactant suspension are stored and transported separately, such that they can be combined prior to use.

2. The vesicular drug delivery system of claim 1, wherein the water-insoluble drug is 17-allylaminogeldanamycin.

3. The vesicular drug delivery system of claim 1, wherein the water insoluble drug is carboxyamidotriazole.

4. The vesicular drug delivery system of claim 1, wherein said water-miscible organic solvent is selected from the group consisting of dimethylformamide, ethanol, glycerin, propylene glycol, and polyethylene glycol.

5. The vesicular drug delivery system of claim 1, wherein said water-miscible organic solvent is dimethylsulfoxide.

6. The vesicular drug delivery system of claim 1, wherein said water-miscible organic solvent is dimethylacetamide.

7. The vesicular drug delivery system of claim 1, wherein the drug solution and the surfactant suspension are sterilized.

8. The vesicular drug delivery system of claim 1, wherein the drug delivery system is physically and chemically stable.

* * * * *